United States Patent
Stoffella

(10) Patent No.: US 6,248,109 B1
(45) Date of Patent: Jun. 19, 2001

(54) IMPLANT FOR INTERCONNECTING TWO BONE FRAGMENTS

(75) Inventor: Rudolf Stoffella, Mödling (AT)

(73) Assignee: Waldemar Link (GmbH & Co.), Hamburg (DE)

( * ) Notice: Subject to any disclaimer, the term of this patent is extended or adjusted under 35 U.S.C. 154(b) by 0 days.

(21) Appl. No.: 09/509,423

(22) PCT Filed: Jul. 2, 1999

(86) PCT No.: PCT/EP99/04630

§ 371 Date: Mar. 28, 2000

§ 102(e) Date: Mar. 28, 2000

(87) PCT Pub. No.: WO00/06036

PCT Pub. Date: Feb. 10, 2000

(30) Foreign Application Priority Data

Jul. 30, 1998 (AT) .................................................. 1317/98

(51) Int. Cl.[7] .................................................. A61B 17/86
(52) U.S. Cl. .................................. 606/75; 606/62; 606/72
(58) Field of Search .................................. 606/60, 62, 67, 606/68, 72, 73, 75

(56) References Cited

U.S. PATENT DOCUMENTS 4,838,254 * 6/1989 Gauthier .
4,915,092 * 4/1990 Firica et al. ........................... 606/67

FOREIGN PATENT DOCUMENTS

000937 U  8/1996  (AT) .
0288229   10/1988 (EP) .

* cited by examiner

Primary Examiner—David O. Reip
(74) Attorney, Agent, or Firm—Morrison & Foerster LLP

(57) ABSTRACT

An implant for fixing two bone fragments to each other comprises a clasp (4) with two arms (7) which are connected to each other at one of their ends and in this area form an eyelet with an opening (8) for passage of a screw (6) which can be screwed into one (3) of the two bone fragments. The free ends of the two arms (7) are introduced into the medullary cavity of the other bone fragment (2) and are anchored therein by spreading apart. To improve the anchoring of the clasp (4) on the bone fragment (3), a shim part (5) is arranged between the clasp (4) and the head (9) of the screw (6), which shim part (5) has a recess for receiving the clasp (4) and is provided with spikes (11) which penetrate into the bone fragment (3).

11 Claims, 1 Drawing Sheet

IMPLANT FOR INTERCONNECTING TWO BONE FRAGMENTS

FIELD OF THE INVENTION

The invention relates to an implant for fixing two bone fragments to each other, in particular for fixing an axially corrected capitulum of a metatarsal bone, e.g. hallux valgus.

BACKGROUND OF THE INVENTION

Osteotomies for treating hallux valgus have already been known for decades and have the object of functionally reconstructing the axis of the 1st metatarsal. It is necessary in this context, after the osteotomy, to fix the two bone fragments in their corrected position in order to prevent mobility between the fragments and to permit reliable osseous union without dislocation.

To fix the osteotomy, it is already known to use plates which are secured to the cortical bone by means of a number of screws in order to prevent the bone fragments from buckling. A considerable surgical outlay is required for this.

Bone clamps are also known for fixing the osteoLomy, but their use involves the risk of splintering of the bone.

AT 937 U has disclosed an implant for fixing two bone fragments to each other, in particular for treating an axial deviation of a metatarsal bone, e.g. hallux valgus, which implant comprises a clasp with two arms which are connected to each other at one of their ends and in this area delimit an opening for passage of a screw which can be screwed into one of the two bone fragments and which, with their other, free ends, can be introduced into the medullary cavity of the other bone fragment and can spread apart. After osteotomy has been performed, the clasp is introduced proximally into the medullary cavity of one bone fragment via the free ends of the two arms and spreads apart in this medullary cavity, after which the clasp is anchored on the other bone fragment by means of the screw guided through the opening.

As a result of the spreading force and the frictional fit of the clasp arms, and as a result of the intermittent compression arising upon functional loading, the intramedullary part of this known implant has a high degree of stability. By contrast, however, the extramedullary part is anchored in the bone via only one screw, whereas a two-point bearing is required on account of the torque which increasingly occurs as the compression of the screw anchoring between implant and metatarsal head decreases.

SUMMARY OF THE INVENTION

The object of the present invention is to improve and stabilize the fixing of this known implant to the one of the two bone fragments connected to the implant via the screw, without in so doing having to modify the surgical procedure. To achieve this object, the invention proposes that a shim part, through which the screw is passed, be arranged between the clasp opening and the screw head, which shim part has projections which can be anchored in the bone fragment. These projections provide for fixing of the clasp to the bone fragment in addition to the screw, as a result of which the stability is considerably improved. The shim part is preferably in the shape of a circular annulus and has spikes protruding essentially at right angles from the annular plane, which spikes penetrate or are pressed into the bone fragment and are thus securely anchored in the bone fragment.

A preferred embodiment of the implant according to the invention is characterized in that the shim part has a recess receiving the clasp with form fit in the area of the opening, and a lateral slot for passage of the arms of the clasp. This embodiment affords a form fit between the shim part and the clasp and thereby reliably prevents the clasp from twisting about the screw axis. The shim part is pressed onto the bone fragment (or vice versa) by the screw, preventing a change in the position of the spikes penetrating into the bone fragment. The invention makes it possible to connect the two bone fragments to each other in a stable manner directly without special bone incision.

It is expedient for the shim part to have at least three projections.

This shim part is preferably made of a tissue-compatible material, for example stainless steel according to ISO 5832/1.

BRIEF DESCRIPTION OF THE DRAWINGS

An illustrative embodiment of the implant according to the invention is shown diagrammatically in the drawings.

DETAILED DESCRIPTION OF THE INVENTION

Figure 1:
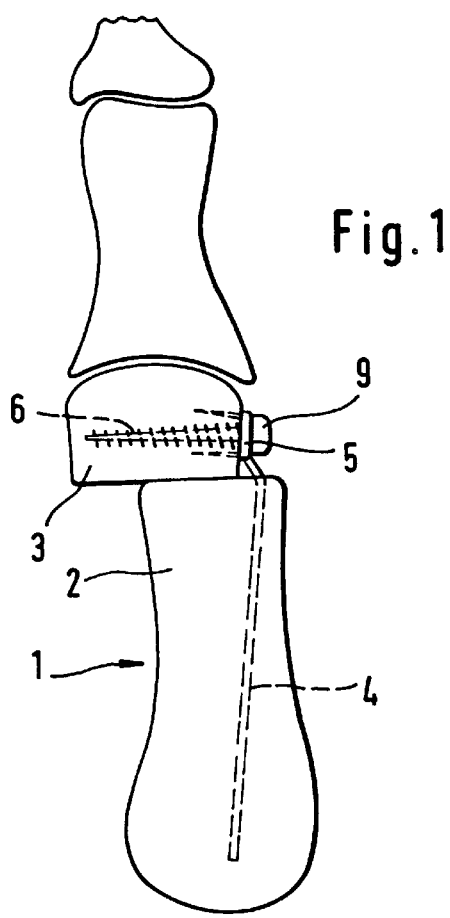
FIG. 1 shows the use of the implant according to the invention in the reconstruction of a hallux valgus.
Figure 3:
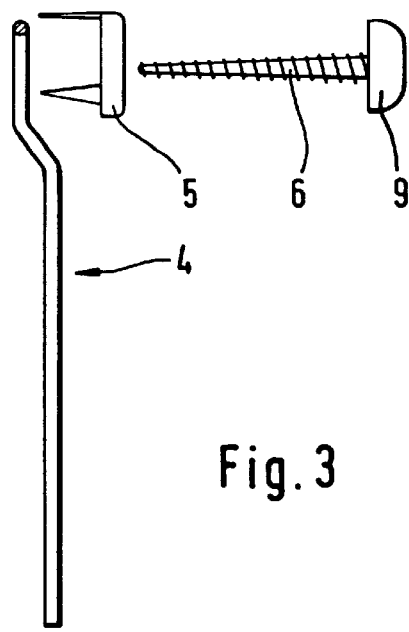
FIG. 3 shows a side view of the individual parts of the implant according to the invention, in an exploded representation.

In FIG. 1, a metatarsal bone 1 is represented following osteotomy and correction, the two bone fragments 2, 3 being fixed by means of an implant according to the invention. This implant according to the invention consists of a clasp 4, a shim part 5 and a bone screw 6.

Figure 2:
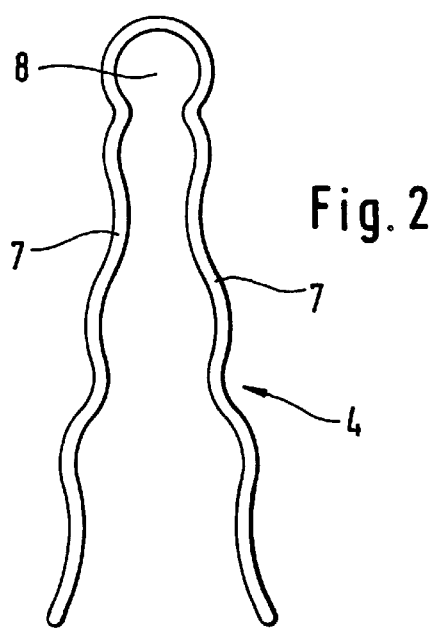
FIG. 2 is a plan view of the clasp forming part of the implant according to the invention.
Figure 4:
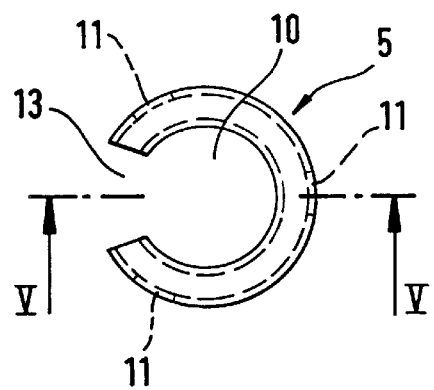
FIG. 4 shows a bottom view of the shim part of the implant according to the invention.
Figure 5:
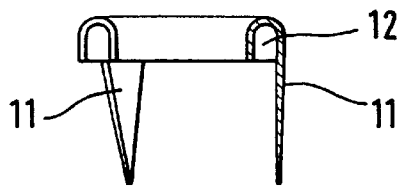
FIG. 5 shows a section along the line V—V in FIG. 4.

As can be seen in particular from FIG. 2, the clasp 4 has two arms 7 which are connected to each other at one of their ends and there delimit an eyelet-shaped opening 8. When the bone fragments 2, 3 are being fixed, the free ends of the two arms 7 are introduced into the medullary cavity of the bone fragment 2 and there take up their spread-apart position shown in FIG. 2, as a result of which the clasp 4 is anchored in this medullary cavity. This anchoring is assisted by an undulating configuration preferably running in the plane of the arms.

The clasp 4 is then anchored in the bone fragment 3 by means of the bone screw 6 which is guided through the opening 8.

According to the invention, the shim part 5 is now arranged between the head 9 of the screw 6 and the clasp 4 in the area of the opening 8, which shim part 5 is of annular design and has an opening 10 whose diameter corresponds approximately to that of the opening 8. This diameter is smaller than the diameter of the head 9 of the screw 6, so that this head 9 bears on the shim part 5.

On the underside the shim part 5 has spikes 11 which, before the bone screw 6 is screwed into the bone fragment 3, are pressed into this bone fragment. The shim part 5 is provided with a recess 12 which is designed as an annular groove and which is adapted to the measurements of the eyelet part of the clasp 4 and receives this area of the opening 8, and it has a lateral slot 13 through which the arms 7 of the clasp 4 can emerge. In this way, the shim part 5 is connected to the clasp 4 with a form fit, and relative movement between the shim part 5 and the clasp 4 is prevented. The shim part 5 is anchored firmly and non-rotatably on the bone fragment 2 by means of the bone screw 6 and the spikes 11. As a result of the form-fit connection between the shim part 5 and the eyelet of the clasp 4, which is maintained between bone surface and screw head by the clamping of these parts, the clasp 4 is thus also prevented from moving relative to the bone fragment.

What is claimed is:

1. Implant for fixing two bone fragments (2, 3) to each other, in particular for fixing an axially corrected capitulum of a metatarsal bone, e.g. hallux valgus, which implant comprises a clasp (4) with two arms (7) which are connected to each other at one of their ends and in this area form an eyelet with an opening (8) for passage of a screw (6) which can be screwed into one (3) of the two bone fragments, and which, with their other, free ends, can be introduced into the other bone fragment (2), wherein a shim part (5), through which the screw (6) is passed, is arranged between the clasp eyelet and the screw head (9), which shim part (5) is provided with projections (11) which can be anchored in the bone fragment (3).

2. Implant according to claim 1, wherein the shim part (5) is in the shape of a circular annulus and the projections are designed as spikes (11) protruding essentially at right angles from the annular plane.

3. Implant according to claim 2, wherein the shim part has a recess receiving the clasp in the area of the eyelet and a lateral slot permitting passage of the arms of the clasp.

4. Implant according to claim 2, wherein the shim part comprises at least three projections.

5. Implant according to claim 2, wherein the shim part is made of a tissue-compatible material.

6. Implant according to claim 1, wherein the shim part (5) has a recess (12) receiving the clasp (4) in the area of the eyelet, and a lateral slot (13) for passage of the arms (7) of the clasp (4).

7. Implant according to claim 6, wherein the shim part comprises at least three projections.

8. Implant according to claim 6, wherein the shim part is made of a tissue-compatible material.

9. Implant according to claim 1, wherein the shim part (5) has at least three projections (11).

10. Implant according to claim 9, wherein the shim part is made of a tissue-compatible material.

11. Implant according to one of claim 1, wherein the shim part (5) is made of a tissue-compatible material.

* * * * *